Figure 1:
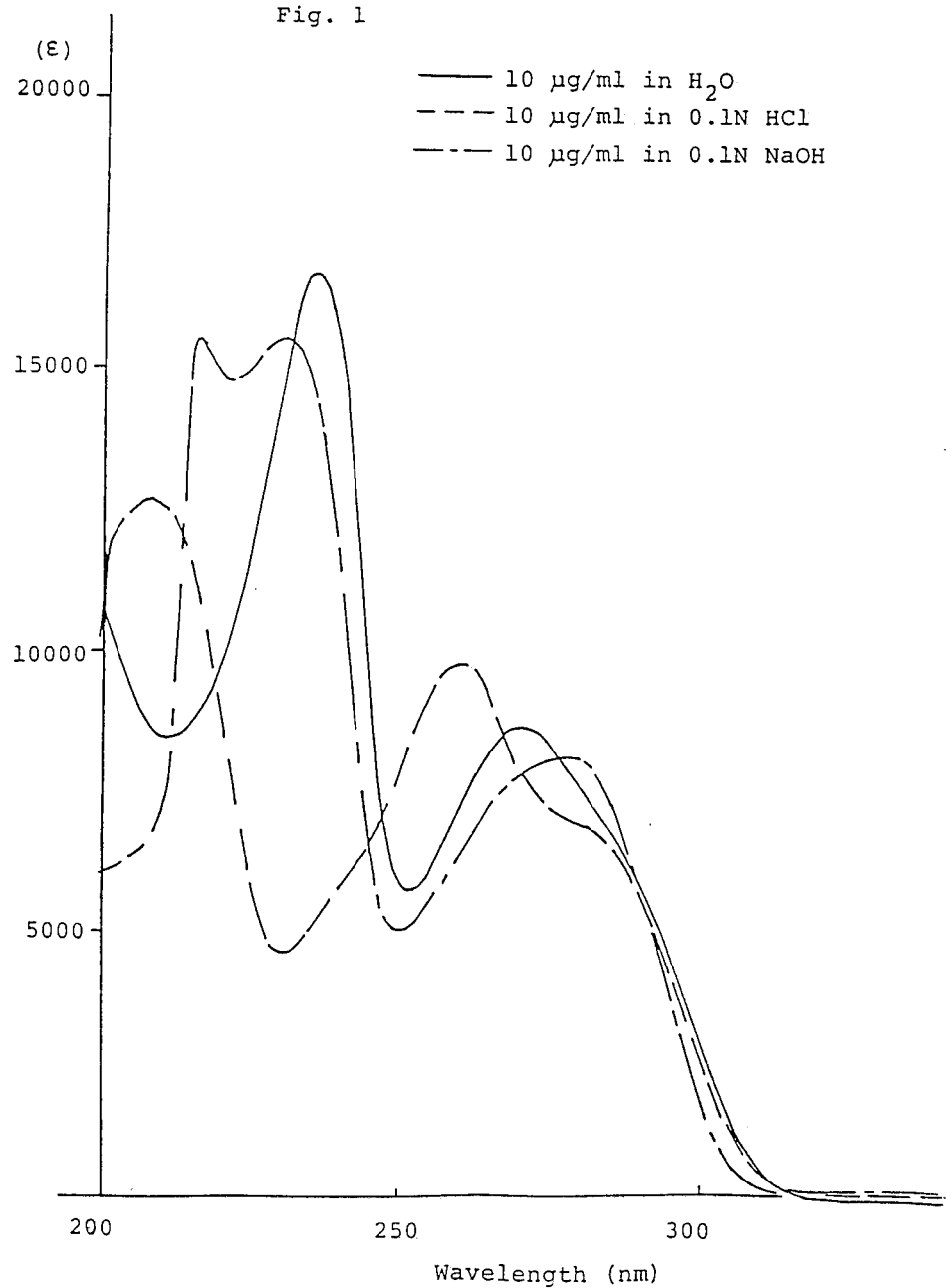

United States Patent [19]

Kitahara et al.

[11] Patent Number: 4,786,723

[45] Date of Patent: Nov. 22, 1988

[54] 7-HYDROXYGUANINE COMPOUNDS, PROCESS FOR PREPARING SAID COMPOUNDS, AND ANTI-TUMOR AGENT CONTAINING THE SAME

[75] Inventors: Mikio Kitahara, Kobe; Kiyoto Ishii, Akashi; Hajime Kawaharada, Kakogawa; Kiyoshi Watanabe, Akashi, all of Japan

[73] Assignee: Kanegafuchi Chemical Industry Co., Ltd., Osaka, Japan

[21] Appl. No.: 844,687

[22] Filed: Mar. 27, 1986

[30] Foreign Application Priority Data

Apr. 8, 1985 [JP] Japan .................................. 60-74979

[51] Int. Cl.⁴ ..................... C07H 17/00; C07H 15/12; C07H 19/06
[52] U.S. Cl. .......................................... 536/24; 536/26
[58] Field of Search ..................................... 536/24, 26

[56] References Cited

FOREIGN PATENT DOCUMENTS 0065300  5/1977  Japan ..................... 536/26
0065298  5/1977  Japan ..................... 536/26
0062295  5/1977  Japan ..................... 536/26
0065299  5/1977  Japan ..................... 536/26

OTHER PUBLICATIONS

Rajabalee et al., Com. J. Chem., vol. 49(11), pp. 1981–1984, 1971.
Fujii et al., Chemistry & Ind., pp. 1598–1599, 9/17/66.

*Primary Examiner*—J. R. Brown
*Assistant Examiner*—L. Eric Crane
*Attorney, Agent, or Firm*—Wegner & Bretschneider

[57] ABSTRACT

Novel 7-hydroxyguanine compounds of the formula:

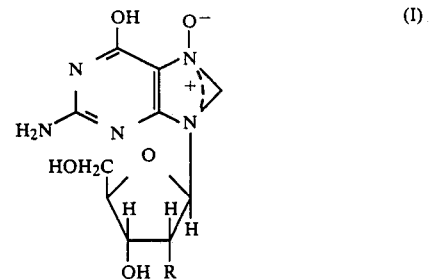

wherein R is hydrogen atom or hydroxy, and a salt thereof, which have excellent anti-tumor activity, process for preparing the compounds, and anti-tumor agent containing said compound as an active ingredient.

4 Claims, 4 Drawing Sheets

7-HYDROXYGUANINE COMPOUNDS, PROCESS FOR PREPARING SAID COMPOUNDS, AND ANTI-TUMOR AGENT CONTAINING THE SAME

This invention relates to novel 7-hydroxyguanine compounds and salts thereof, a process for preparing the compounds, and an anti-tumor agent containing the compound as an active ingredient. More particularly, it relates to novel 7-hydroxyguanine compounds of the formula:

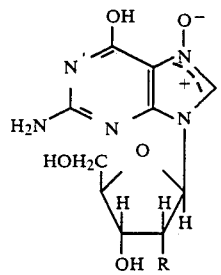

(I)

wherein R is hydrogen or hydroxy, and salts thereof with a compound being capable of producing a salt with said compounds, a process for preparing the compounds, and an anti-tumor agent or composition containing such compound as an active ingredient.

It has been found that among various derivatives prepared by chemical or enzymatic modification of 7-hydroxyguanine of the formula:

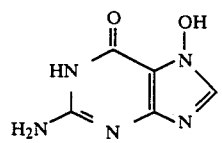

(II)

the compounds of the above formula (I) and a salt thereof have excellent anti-tumor activity.

The compounds of the formula (I) are all amphoteric compounds and can form a salt with a base or acid, and the salts of the compounds (I) in the present invention include salts with a compound being capable of forming a salt therewith. Suitable examples of the salts with a base are (i) salts with alkali metals or alkaline earth metals, (ii) ammonium salt, (iii) salts with amines, particularly salts with ethylamine, dimethylamine, piperidine, morpholine, etc. Suitable examples of the salts with an acid are (i) salts with mineral acids, particularly, hydrochloride, hydroiodide, or sulfate, (ii) salts with organic acids, particularly benzenesulfonate, p-toluenesulfonate, naphthalenesulfonate, acetate, propionate, citrate, malonate, etc. These salts are preferably a pharmacologically acceptable salt in order to use the compounds as an anti-tumor agent.

Particularly suitable examples of the compounds in the present invention are shown in the following Table 1.

TABLE 1

|  | Compound A | Compound B |
| --- | --- | --- |
| R | OH | H |
| Molecular formula | $C_{10}H_{13}N_5O_6$ | $C_{10}H_{13}N_5O_5$ |
| Melting point | 138–139° C. (dec.) | 136–137° C. (dec.) |
| Elementary analysis | For $C_{10}H_{13}N_5O_6$ Found (Calcd.) C 39.98 (40.14) H 4.31 (4.32) N 23.45 (23.40) | For $C_{10}H_{13}N_5O_5.H_2O$ Found (Calcd.) C 40.03 (39.87) H 5.12 (5.02) N 23.40 (23.25) |
| UV spectrum | FIG. 1 | FIG. 3 |
| IR spectrum | FIG. 2 | FIG. 4 |

The compounds (I) of the present invention can be prepared by reacting 7-hydroxyguanine (II) with a pentose-1-phosphoric acid of the formula:

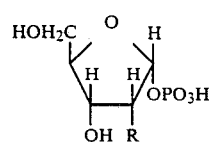

(II)

wherein R is as defined above, in the presence of nucleoside phosphorylase or a microorganism being capable of producing nucleoside phosphorylase.

The 7-hydroxyguanine (II) used as a substrate can be prepared from a culture broth of Streptomyces sp A-347 (which has been deposited as FERM BP-541 at Fermentation Research Institute, Agency of Industrial Science and Technology, Japan under the Budapest Treaty) by the method as disclosed in Preparation hereinafter. Besides, the pentose-1-phosphoric acid (III) or a salt thereof includes 2-deoxyribose-1-phosphoric acid and α-D-ribose-1-phosphoric acid, and salts of these acids. These compounds are commercially available or can be prepared by treating the corresponding pentose-containing nucleoside with nucleoside phosphorylase [cf. Methods in Enzymology, Vol. 3, pages 181–186, 1957]

The nucleoside phosphorylase includes all substances having nucleoside phosphorylase activity, such as purified nucleoside phosphorylase, crude nucleoside phosphorylase, and nucleoside phosphorylase-containing substances, which are obtained from a wide range of organisms such as animals, microorganisms. There is also commercially available, for example, Nucleoside Phosphorylase (manufactured by Sigma Co., U.S.A., from bovine spleen). Instead of the enzyme, there can also be used microorganisms being capable of producing nucleoside phosphorylase, or culture broth or cultivated cells thereof. Such microorganisms include those of the genus Achromobacter, Aeromonas, Bacillus, Brevibacterium, Citrobacter, Enterobacter, Erwinia, Escherichia, Hafnia, Klebsiella, Proteus, Pseudomonas, and Serratia. Suitable examples of the microorganisms are *Achromobacter xerosis* IFO 12668, *Aeromonas hydrophila* IFO 3820, *Bacillus sphaerius* IFO 3525, *Brevibacterium acetylicum* IFO 12146, *Citrobacter freundii* IFO 12681, *Enterobacter aerogenes* IFO 13534, *Enterobacter cloacae* IFO 3320, *Erwinia carotovora* IFO 12380, *Escherichia coli* IFO 3301, *Hafnia alvei* IFO 3731, *Klebsiella pneumoniae* IFO 3321, *Proteus vulgaris* IFO 3851, *Pseudomonas stutzeri* IFO 13596, *Serratia marcescens* IFO 3054, and the like.

These microorganisms can be cultured in a conventional nutrient medium containing, for example, glucose, peptone, yeast extract, meat extract, etc. at a culture temperature of 10° to 40° C., preferably 25° to 35° C., at a pH 3 to 8, preferably pH 6–7, under an aerobic condition for 24 to 48 hours. The microorganisms may be used in the present invention in various forms, such as the culture per se, culture broth, cultivated cells, filtrate of the culture broth, and the like.

The substances having nucleoside phosphorylase activity are preferably used together with a buffer solution not only in the case of enzyme (purified or crude) but also in the case of microorganisms or culture products thereof in view of the purification of the reaction product. The buffer solution includes inorganic salt buffers (e.g. Tris-HCl buffer), organic acid salt buffers (e.g. sodium acetate buffer, sodium citrate buffer). Concentration of the buffer may vary depending on the kinds of buffer, but is usually in the range of 10 mM to 500 mM, preferably 50 mM to 100 mM.

The enzymatic reaction of the compound (II) and the compound (III) can usually be carried out by suspending the substrate compound (II) (i.e. 7-hydroxyguanine) in an amount of 0.05 to 0.2% (w/v %) and the compound (III) (i.e. pentose-1-phosphoric acid) in an amount of 0.05 to 0.4% (w/v %) in a buffer and thereto adding an enzyme in an appropriate amount, for example, in a weight ratio of the enzyme: the substrate compound (II) of 1:20 to 1:1,000, and subjecting the mixture to reaction at a temperature of 10° to 65° C., preferably 40° to 60° C. The amount of the remaining substrate compound (II) and the produced compound (I) in the reaction mixture is checked by high performance liquid chromatography (HPLC); when the amount of the produced compound (I) no longer increases, the reaction can be stopped. The enzymatic reaction is usually carried out at pH 6 to 8, preferably pH 6.5 to 7.5.

When an enzyme produced by a microorganism is used, it is usually used in the form of a crude enzyme solution which is prepared by culturing the microorganism as mentioned hereinbefore, collecting cells from the culture broth, washing the cells with a physiological saline solution, fracturing the cells by ultrasonic fracture, centrifuging the fractured cells to obtain a supernatant fluid. The cells of the culture may also be used as they stand. Moreover, the enzyme or cells of microorganisms may be immobilized by a conventional immobilization method, by which the enzyme or cells can repeatedly be used.

The compound (I) thus obtained can easily be isolated from the reaction mixture by utilizing the amphoteric property. That is, the produced compound (I) can be collected from the reaction mixture with various adsorbents. The adsorbents include active carbon, strongly acidic cation exchange resins, weakly basic anion exchange resins, and the like. Particularly effective purification is carried out by passing the reaction mixture through a nickel type column packed with a chelate resin such as Chelex ® 100 (manufactured by Bio-Rad Co., U.S.A.) and then eluting the adsorbed material with a diluted alkali. It is also effectively purified by a column chromatography using a gel filtration carrier such as Sephadex ® G-10 or Sephadex ® LH-20 (manufactured by Pharmacia, Sweden). By combination of the conventional purification methods or by repeating the purification, the desired compound (I) can be obtained in high purity. Pure compound (I) can also be obtained by crystallization from a mixed solvent such as water-methanol.

The compounds (I) or a salt thereof of this invention show excellent anti-tumor activities against various tumors such as Hodgkin's disease, reticulosarcoma, leukemia, multiple myeloma, deciduocellular sarcoma, lung cancer, mammary cancer, ovary cancer, uterine cancer, stomach cancer, hepatic cancer, skin cancer, and the like. The representative anti-tumor activity is illustrated by the following experiment.

EXPERIMENT 1

Anti-tumor activity against L-1210 leukemia in mice $BDF_1$ female mice weighing 18–23 g (one group: 3 mice) were used. The mice were intraperitoneally inoculated with mouse L-1210 leukemia cells ($1 \times 10^5$). From the next day after inoculation of leukemia cells, a solution or suspension of a test compound in 50 mM phosphate buffer (pH 7.4) was intraperitoneally administered for 5 days in a dose as shown in Table 2, and the survival days of mice was measured. As a control, 50 mM phosphate buffer (pH 7.4) without a test compound was intraperitoneally administered likewise. Based on the data, the life-prolongation ratio of the test compound was calculated. The results are shown in Table 2.

TABLE 2

| Dose (mg/kg/day) | Life-prolongation ratio* |  |
|---|---|---|
|  | Compound A | Compound B |
| 1.0 | 128.9 | 120.5 |
| 4.0 | 148.2 | 160.2 |
| 16.0 | 148.2 | 168.7 |

*Life-prolongation ratio (%) = $\dfrac{\text{Average survival days of treated mice}}{\text{Average survival days of untreated mice}} \times 100$ The test compounds shown in Table 2 correspond to those in Table 1.

As is clear from the experimental results in Table 2, the compounds of this invention show excellent anti-tumor activity.

EXPERIMENT 2

Acute toxicity

ICR male mice weighing 18–23 g were intraperitoneally administered with the test compounds for one week, and the 50% lethal toxicity ($LD_{50}$: mg/kg) was measured by a conventional method. As a result, Compound A and Compound B showed $LD_{50}$ of 192.0 mg/kg and 172.5 mg/kg, respectively.

The compounds (I) or a pharmaceutically acceptable salt thereof can be used as an anti-tumor agent for the prophylaxis or treatment of tumors in animals including the human being. The compounds (I) or a salt thereof are usually used in the form of a pharmaceutical composition. The composition includes conventional pharmaceutical preparations, for example, solid preparations such as tablets, pills, capsules, granules, fine granules, powders, etc. and liquid preparations such as solutions, suspensions, injections. The compositions can be prepared by admixing the active compound (I) or a pharmaceutically acceptable salt thereof with a conventional pharmaceutically acceptable carrier or diluent in a usual manner. The pharmaceutically acceptable carriers or diluents used from the oral preparations include, for example, binding agents (e.g. syrup, gum arabic, gelatine, sorbitol, tragacanth, polyvinylpyrrolidone, etc.), excipients (e.g. lactose, sucrose, corn starch, potassium phosphate, sorbitol, etc.), lubricants (e.g. magnesium stearate, talc, polyethylene glycol, silica, etc.), disintegrators (e.g. potato starch, etc.), wetting agents (e.g. sodium laurylsulfate, etc.). For parenteral administration, they may be used in the form of an injection, solution, suspension, or emulsion in admixture with conventional pharmaceutically acceptable carrier or diluents suitable for the parenteral administration, such as physiological saline solution, glycerin, propylene glycol, simple syrup, ethanol, fatty oils, ethylene glycol, sorbitol, or the like. The pharmaceutical compositions contains the active compound (I) or a salt thereof in an amount of 10 to 800 mg, preferably 20 to 200 mg, in a dosage unit and may also contain other medicaments than the active compounds (I) or a salt thereof.

The compositions of this invention can be administered in oral or parenteral route.

The compounds (I) or a salt thereof of this invention are used in a dose effective for the prophylaxis or treatment of tumors without undesirable side effect. The dose may vary depending on the age, weight and sex of patient, administration route, severity of disease, and the like, and the most effective dose may be decided by doctors, but it is usually in a range of 10 to 800 mg per day in adult.

The present invention is illustrated by the following Preparation and Examples, but should not be construed to be limited thereof.

PREPARATION 1

Preparation of substrate (7-hydroxyguanine):

Streptomyces sp. A-347 strain (FERM BP-541) which is previously cultured on a slant agar medium is inoculated into a 500 ml flash which contains a liquid medium (pH 7.4, 100 ml) containing glucose 2.0%, sucrose 1.0%, soy bean powder 2.0% and calcium carbonate 0.3%, and it is cultured on a rotary shaking machine at 28° C. for 48 hours to give a seed liquid culture.

180 ml of the seed liquid culture obtained above is inoculated into a 30 liter jar fermentor containing the same liquid medium as above (18 liter), and it is cultured at 28° C. for 90 hours (agitation speed: 350 r.p.m., aeration volume: 9 liter/minute). The cultures obtained in two fermentors are combined and regulated to pH 3.2 with 5N hydrochloric acid, and then centrifuged to give a culture filtrate. The filtrate is regulated to pH 5.2 with 5N sodium hydroxide solution (volume: 27.5 liter, content of the compound: 100 µg/ml). The culture filtrate (27.5 liter) is passed through a column (8.4 cm×60 cm) packed with Amberlyst ® 15 (H+ type) (4.0 liter) to adsorb the compound thereto. The column is washed with water (8 liter) and eluted with 0.5N aqueous ammonia to give an eluate fraction containing the compound (8 liter). This fraction is concentrated under reduced pressure to remove ammonia, and thereto is added deionized water so as to make totally 15 liter (content of the compound: 158 µg/ml).

The solution (15 liter) obtained above is passed through a column (6 cm×35 cm) packed with Amberlite ® IRA-45 (OH− type) (1 liter) to adsorb the compound, and the column is eluted with 0.3N aqueous ammonia to give an active fraction (1 liter). This fraction is concentrated under reduced pressure to remove ammonia and thereto is added deionized water so as to make totally 3 liter (content of the compound: 700 µg/ml).

The solution (3 liter) thus obtained is subjected to ion exchange chromatography using a column (inner diameter: 3 cm, volume: 300 ml) packed with DEAE-Sephadex ® A-25 ($HCO_3^-$ type), and the column is washed with 0.05M aqueous ammonium bicarbonate (300 ml) and then eluted with 0.2M aqueous ammonium bicarbonate to give fractions (each 10 ml). The 50th to 95th fractions are combined and concentrated under reduced pressure at 60° C. to precipitate crude powder of 7-hydroxyguanine (1412 mg, 991 µg/ml). The crude powder of 7-hydroxyguanine (1035 mg) is dissolved in 5N aqueous ammonia (45 ml) at 60° C., and the mixture is allowed to stand in cooled place (5° C.) overnight. The precipitated crystals are separated by filtration to give pure 7-hydroxyguanine (636.3 mg, 1,000 µg/ml) as plates.

m.p. >300° C.

Molecular weight: 167 (FD-MS, m/z 167; M+)

Elementary analysis for $C_5H_5N_5O_2$: Calcd. (%): C, 35.95; H, 3.02; N, 41.90: Found (%): C, 35.08; H, 3.10; N, 40.92.

EXAMPLE 1

7-Hydroxyguanine [Compound (II)] (800 mg) and barium ribose-1-phosphate (2.2 g) are dissolved in 40 mM sodium citrate buffer (pH 6.5, 1.0 liter) and thereto is added purine nucleoside phosphorylase (obtained from bovine spleen, manufactured by Sigma Co., U.S.A., 440 unit), and the mixture is reacted at 40° C. for 9 hours. The reaction mixture is regulated to pH 9.5 with 28% aqueous ammonia and then concentrated under reduced pressure so as to make totally 40 ml. The mixture is subjected to a column chromatography with Sephadex ® G-10. After eluting with water, the eluate is concentrated and further subjected to column chromatography with Sephadex ® LH-20. After eluting with 0.05N aqueous ammonia, the eluate is concentrated to dryness to give white powder (700 mg). The powder (700 mg) is crystallized from water-methanol (1:1) (5 ml) to give the desired 7-hydroxyguanine riboside (Compound A) (326 mg) as colorless needles.

m.p. 138°–139° C. (dec.)

Elementary analysis for $C_{10}H_{13}N_5O_6$: Calcd. (%): C, 40.14; H, 4.32; N, 23.40: Found (%): C, 39.98; H, 4.31; N, 23.45.

Figure 2:
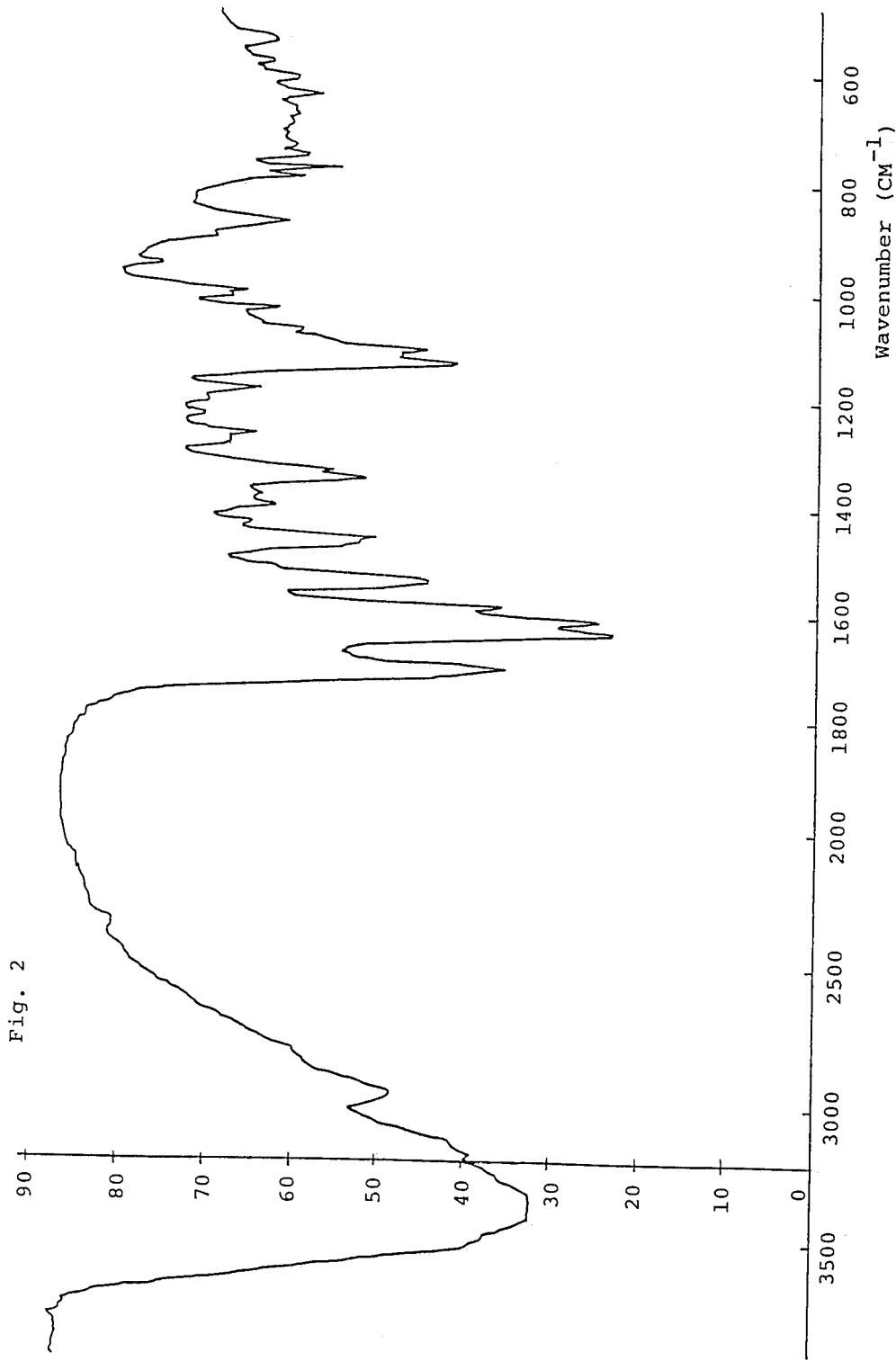

UV spectrum and IR spectrum are as shown in FIG. 1 and FIG. 2, respectively.

EXAMPLE 2

7-Hydroxyguanine [Compound (II)] (170 mg) and barium deoxyribose-1-phosphate (1.0 g) are dissolved in 50 mM sodium citrate buffer (pH 6.5, 600 ml) and thereto is added purine nucleoside phosphorylase (origined from bovine spleen, manufactured by Sigma Co., U.S.A., 200 unit), and the mixture is reacted at 40° C. for 50 minutes. The reaction mixture is ice-cooled, and centrifuged at 3,000 r.p.m. to remove the precipitates. The supernatant is passed through a nickel type column (400 ml) packed with Chelex ® 100 (manufactured by Bio-Rad Co., U.S.A.) After washing with water, the column is eluted with 0.5N aqueous ammonia (600 ml). The eluate is subjected to column chromatography with Amberlite ® IRC-50 (manufactured by Rohm & Haas, U.S.A., NH4 type). After eluting with water, the eluate is concentrated to dryness to give white powder (170 mg). The powder (170 mg) is crystallized from 0.05N aqueous ammonia (3 ml) to give the desired 7-hydroxyguanine deoxyriboside (Compound B) (130 mg) as colorless needles.

m.p. 136°–137° C. (dec.)

Elementary analysis for $C_{10}H_{13}N_5O_5 \cdot H_2O$: Calcd. (%): C, 39.87; H, 5.02; N, 23.25: Found (%): C, 40.03; H, 5.12; N, 23.40.

Figure 3:
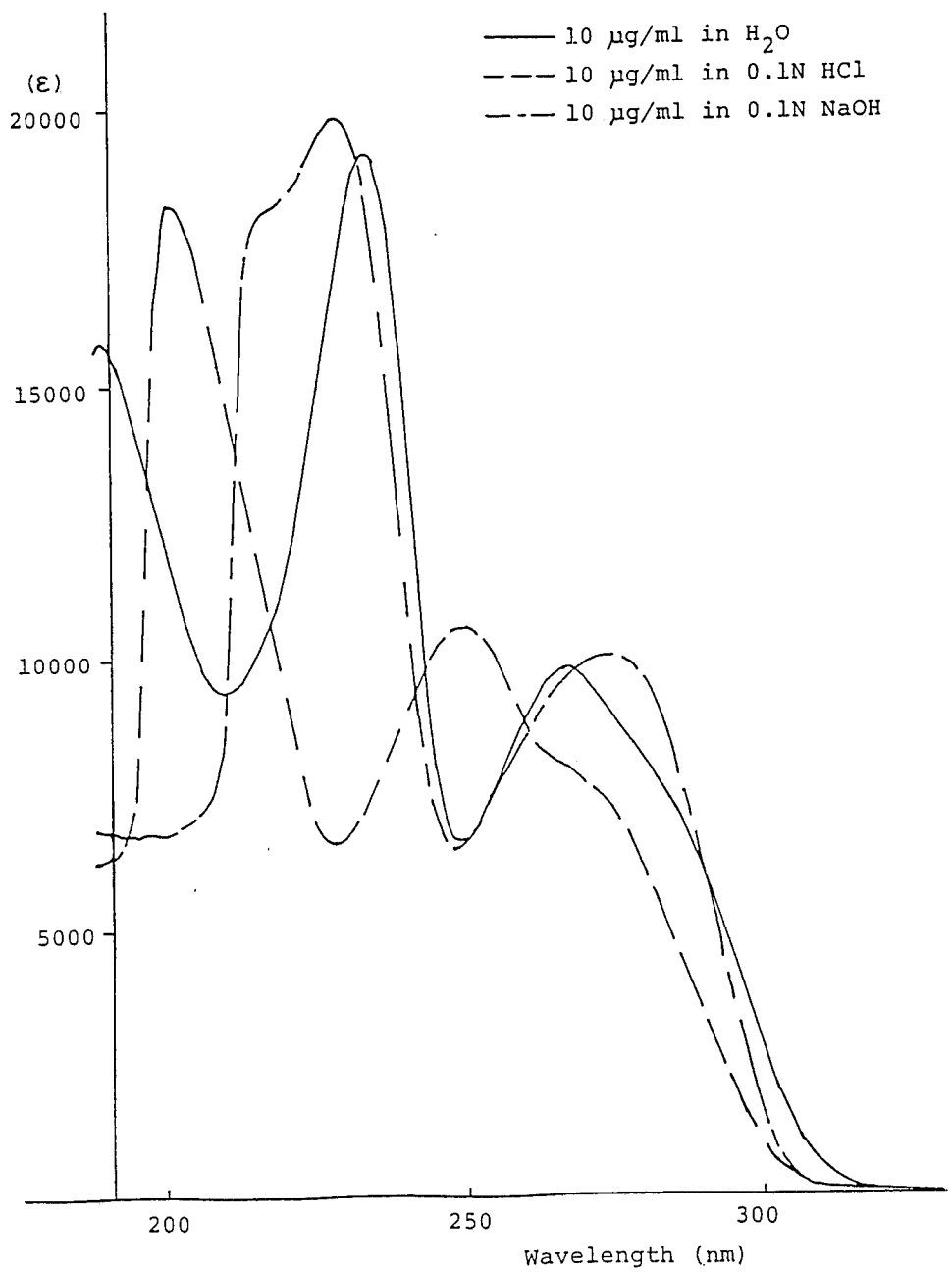
Figure 4:
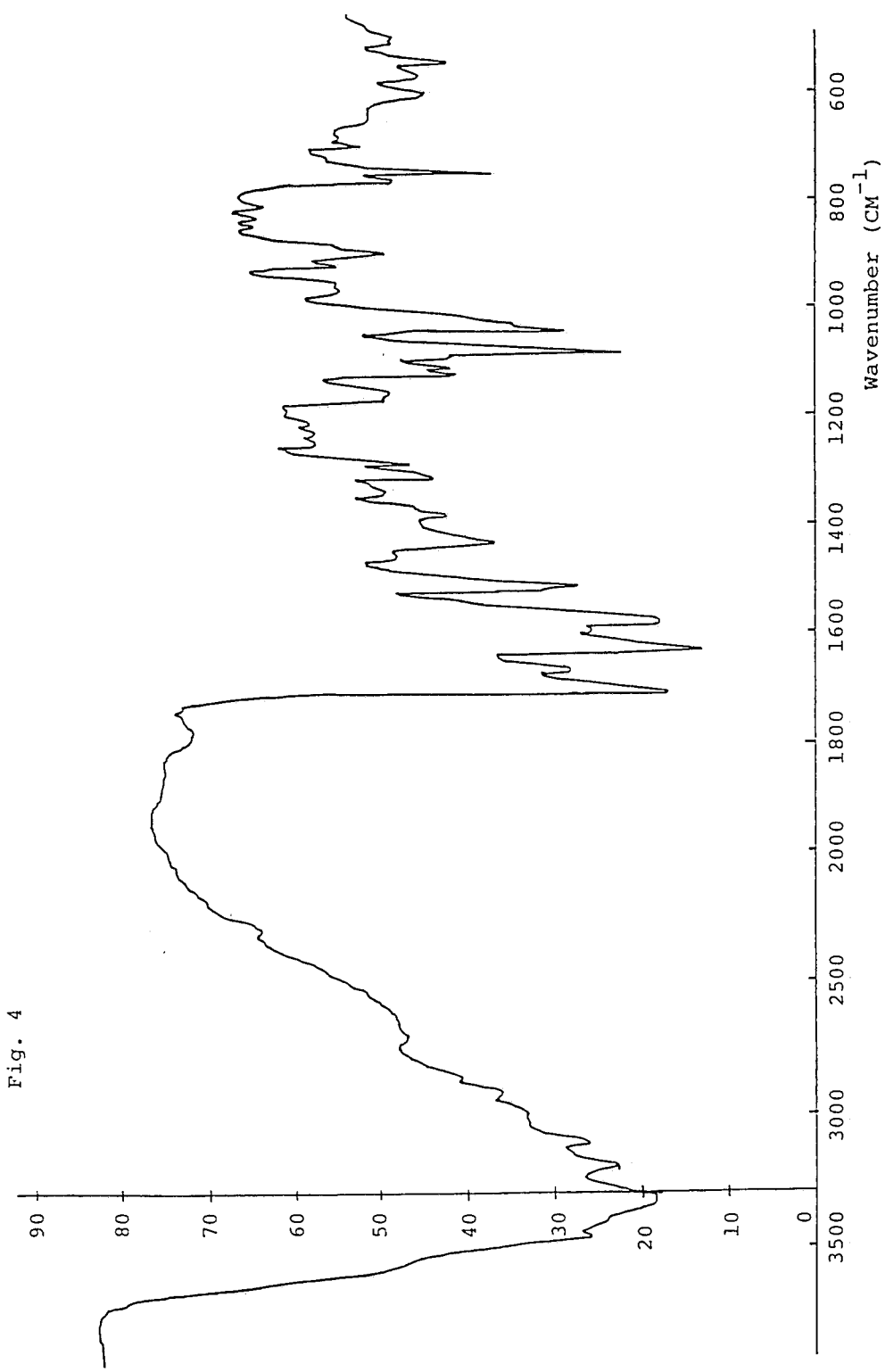

UV spectrum and IR spectrum are as shown in FIG. 3 and FIG. 4, respectively.

EXAMPLE 3

A liquid medium (pH 7.2, 100 ml) containing peptone 1%, meat extract 1.0%, yeast extract 0.5% and sodium chloride 0.5% is sterilized in a 500 ml Sakaguchi flask at 120° C. for 20 minutes. The medium is inoculated with the microorganisms as shown in Table 3 (each one platinum loop), and the microorganisms are each shake-cultured at 30° C. for 24 hours. The cells are collected from the culture broth by centrifugation, washed with a physiological saline solution and then suspended in distilled water in a concentration of 50% (w/v %). The suspension is treated with ultrasonic for 2.5 minutes, and then centrifuged at 10,000 g for 20 minutes. The supernatant thus obtained is used as a crude enzyme solution.

The crude enzyme solution (0.1 ml) obtained above is added to a mixture containing 0.4M Tris-HCl buffer (pH 7.5, 0.1 ml), 10 mM 7-hydroxyguanine (0.1 ml), and 20 mM ribose-1-phosphoric acid or deoxyribose-1-phosphoric acid (0.1 ml). The mixture is kept at 40° C. for 4 hours, and 7-hydroxyguanine riboside or 7-hydroxyguanine deoxyriboside produced in the reaction mixture is set and measured by high performance liquid chromatography (using type 5 device, manufactured by Nihon Bunko K.K., Japan, and Partisil ® 10 SCX column, manufactured by Chemuco K.K., Japan). The results are shown in Table 3.

The high performance liquid chromatography (HPLC) is carried out under the following conditions:

Column: Partisil ® 10 SCX, 4.6×250 mm (manufactured by Chemuco K.K., Japan)

Mobile phase: 10 mM NH4H2PO4 buffer (pH 2.9)

Flow rate: 1.0 ml/minute

Detection: at UV 254

Device: type 5 device, manufactured by Nihon Bunko k.k., Japan

Under the above conditions, 7-hydroxyguanine, Compound A (7-hydroxyguanine riboside) and Compound B (7-hydroxyguanine deoxyriboside) show the peak at the retention time of 10 minutes, 5.0 minutes and 6.8 minutes, respectively.

TABLE 3

| Microorganisms | Compound A (7-hydroxyguanine riboside) (μg/ml) | Compound B (7-hydroxyguanine deoxyriboside) (μg/ml) |
| --- | --- | --- |
| *Achromobacter xerosis* IFO 12668 | 10.1 | 15.3 |
| *Aeromonas hydrophila* IFO 3820 | 69.9 | 126.8 |
| *Bacillus sphaerius* IFO 3525 | 93.7 | 312.0 |
| *Brevibacterium acetylicum* IFO 12146 | 189.7 | 180.3 |
| *Citrobacter freundii* IFO 12681 | 7.2 | 27.9 |
| *Enterobacter aerogenes* IFO 13534 | 23.7 | Not detected |
| *Enterobacter cloacae* IFO 3320 | 16.9 | Not detected |
| *Erwinia carotovora* IFO 12380 | 138.7 | 213.1 |
| *Escherichia coli* IFO 3301 | 112.2 | 5.5 |
| *Hafnia alvei* IFO 3731 | 47.0 | Not detected |
| *Klebsiella pneumoniae* IFO 3321 | 40.2 | Not detected |
| *Proteus vulgaris* IFO 3851 | 266.9 | 76.0 |
| *Pseudomonas stutzeri* IFO 13596 | 161.2 | 178.1 |
| *Serratia marcescens* IFO 3054 | 38.6 | Not detected |

What is claimed is:

1. A 7-hydroxyguanine compound of the formula:

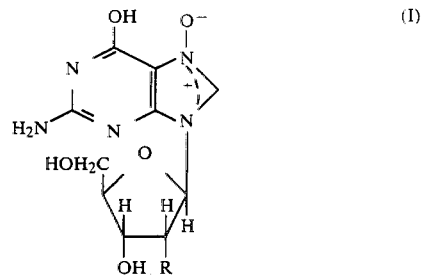

wherein R is hydrogen or hydroxy, and a salt thereof.

2. The compound according to claim 1, wherein R is hydrogen.

3. The compound according to claim 1, wherein R is hydroxy.

4. An anti-leukemia composition which comprises as an active ingredient an effective amount of a 7-hydroxyguanine compound of the formula:

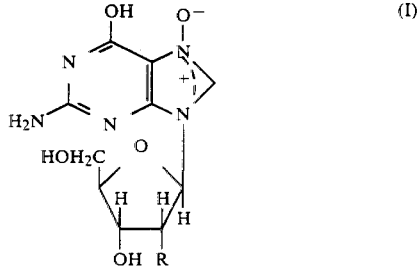

wherein R is hydrogen or hydroxy, or a pharmaceutically acceptable salt thereof in admixture with a pharmaceutically acceptable carrier or diluent.

* * * * *